(12) United States Patent
Mandell

(10) Patent No.: US 7,542,804 B2
(45) Date of Patent: Jun. 2, 2009

(54) NEUROMUSCULAR STIMULATION TO AVOID PULMONARY EMBOLISMS

(75) Inventor: Lee J. Mandell, West Hills, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 0 days.

(21) Appl. No.: 11/004,369

(22) Filed: Dec. 3, 2004

(65) Prior Publication Data

US 2006/0122663 A1    Jun. 8, 2006

(51) Int. Cl.
*A61N 1/08* (2006.01)
(52) U.S. Cl. .............. 607/48; 607/2; 607/3; 607/46; 607/49; 607/61; 600/546; 600/595
(58) Field of Classification Search ............ 607/2–3, 607/46, 48–49, 61; 600/546, 595
See application file for complete search history.

(56) References Cited

U.S. PATENT DOCUMENTS

| | | | |
|---|---|---|---|
| 5,193,539 A | | 3/1993 | Schulman et al. |
| 5,193,540 A | | 3/1993 | Schulman et al. |
| 5,304,206 A | * | 4/1994 | Baker et al. ............... 607/2 |
| 5,324,316 A | | 6/1994 | Schulman et al. |
| 5,759,198 A | * | 6/1998 | Karell .................... 607/48 |
| 5,843,142 A | * | 12/1998 | Sultan .................... 607/49 |
| 6,164,284 A | | 12/2000 | Schulman et al. |
| 6,185,452 B1 | | 2/2001 | Schulman et al. |
| 6,208,894 B1 | | 3/2001 | Schulman et al. |
| 6,282,448 B1 | * | 8/2001 | Katz et al. ............... 607/48 |
| 6,315,721 B2 | | 11/2001 | Schulman et al. |
| 6,466,821 B1 | | 10/2002 | Pianca et al. |
| 6,472,991 B1 | | 10/2002 | Schulman et al. |

(Continued)

FOREIGN PATENT DOCUMENTS

DE    3932405    4/1991

OTHER PUBLICATIONS

Troyk, et al, Development of Bion Technology for Functional Electrical Stimulation: BiDirectional Telemetry, 2001 Proceedings of the 23rd Annual EMBS International Conference, Oct. 25, 2001, pp. 1317-1320, Publisher: IEEE, Published in: Istanbul, Turkey.

(Continued)

*Primary Examiner*—Carl H Layno
*Assistant Examiner*—Deborah Malamud
(74) *Attorney, Agent, or Firm*—Malcolm J. Romano

(57) ABSTRACT

A system and method that provide a prophylactic treatment to a person, e.g., a patient, to avoid the occurrence of pulmonary embolisms by the system providing neuromuscular stimulation to a person's lower extremities, e.g., the person's legs, when the system senses that a person has been immobile for an extended period of time. An implantable neuromuscular pacer, such as that described in U.S. Pat. Nos. 5,193,539; 5,193,540; 6,164,284; 6,185,452; 6,208,894; 6,315,721; 6,564,807; and their progeny, may be used to provide to selectively provide such stimulation. Preferably, such a device may be battery powered so that it can operate independent of an external apparatus. In particular, systems and devices of the present invention preferably additionally include an activity monitor, e.g., an accelerometer or the like, that disables or limits stimulation to pronged time periods in which there is limited activity.

26 Claims, 14 Drawing Sheets

U.S. PATENT DOCUMENTS

| | | |
|---|---|---|
| 6,564,807 B1 | 5/2003 | Schulman et al. |
| 6,738,672 B2 | 5/2004 | Schulman et al. |
| 6,804,558 B2 | 10/2004 | Haller et al. |
| 6,845,267 B2 | 1/2005 | Harrison et al. |
| 2002/0193859 A1 | 12/2002 | Schulman et al. |
| 2003/0078618 A1 | 4/2003 | Fey et al. |
| 2003/0078634 A1* | 4/2003 | Schulman et al. ............. 607/61 |
| 2003/0078643 A1 | 4/2003 | Schulman et al. |
| 2003/0083698 A1* | 5/2003 | Whitehurst et al. ............ 607/3 |
| 2003/0195578 A1 | 10/2003 | Perron et al. |
| 2004/0082978 A1 | 4/2004 | Harrison et al. |
| 2004/0153127 A1 | 8/2004 | Gordon et al. |
| 2004/0158294 A1 | 8/2004 | Thompson |
| 2004/0183607 A1 | 9/2004 | Moore |
| 2004/0225335 A1 | 11/2004 | Whitehurst et al. |
| 2005/0021108 A1 | 1/2005 | Klosterman et al. |
| 2005/0209644 A1* | 9/2005 | Heruth et al. ................. 607/3 |

OTHER PUBLICATIONS

Loeb, et al, Bion System for Distributed Neural Prosthetic Interfaces, 2001, pp. 1-23, Publisher: Journal of Medical Engineering and Physics, Published in: Los Angeles, CA.

Loeb, Bion Development at AMI: Clinical Technical Progress, Bion Development at AMI: Clinical Technical Progress, Sep. 6, 2004, Published in: Los Angeles.

* cited by examiner

OPEN LOOP CONTROL/MONITOR

CLOSED LOOP CONTROL

EXEMPLARY INJURY

COORDINATED CLOSED LOOP HAND CONTROL

NEUROMUSCULAR STIMULATION TO AVOID PULMONARY EMBOLISMS

FIELD OF THE INVENTION

The present invention is generally directed to a system which provides a prophylactic treatment to a person to avoid creation of pulmonary embolisms by neuromuscular stimulation to a person's lower extremities, e.g., the person's legs, when the system senses that the person has been immobile for an extended period of time.

BACKGROUND OF THE INVENTION

Certain medical conditions are known to exist that make individuals prone to pulmonary embolisms. These conditions include susceptibility to deep vein thrombosis resulting from prolonged immobility (potentially exacerbated by lack of fluids). The unexpected death in 2003 of journalist David Bloom (being in a relatively immobile and most likely in a somewhat dehydrated condition while in a military type vehicle during the 2003 war in IRAQ) and unexpected attacks in 1994 and 1998 (both non-fatal) reportedly experienced by Vice President Dan Quayle from a prolonged air flight (due to a condition sometimes referred to as "economy class syndrome" in reference to seating with limited leg room in economy class but equally applicable to any relatively immobile seating or position) demonstrate anyone's susceptibility to such conditions. While it has been recommended that passengers periodically move around the cabin during prolonged air flights to avoid such problems, the capability of an individual to move sufficiently to avoid such problems may be limited or impossible, e.g., in a war environment.

SUMMARY OF THE INVENTION

The present invention is directed to a system and method that provide a prophylactic treatment to a person, e.g., a patient, to avoid the occurrence of pulmonary embolisms by providing neuromuscular stimulation to a person's lower extremities, e.g., the person's legs, when the system senses that the person has been immobile for an extended period of time. An implantable neuromuscular pacer may be used to selectively provide such stimulation. Such implantable devices are described in U.S. Pat. Nos. 5,193,539; 5,193,540; 6,164,284; 6,185,452; 6,208,894; 6,315,721; 6,564,807; and their progeny, each of which is incorporated herein by reference in its entirety. Such a device may be referred to as a BION®, a trademark of Advanced Bionics Corporation. Preferably such a device may be battery powered so that it can operate independent of an external apparatus. In particular, devices and systems of the present invention preferably additionally include an activity monitor, e.g., an accelerometer or the like (see U.S. Pat. No. 6,466,821 which is incorporated herein by reference), that disables or limits stimulation to pronged time periods in which there is limited activity.

Implanted devices for use in embodiments of the present invention may be configured similarly to the devices described in the commonly owned U.S. Pat. No. 6,164,284 (hereinafter referred to as the '284 patent), incorporated herein by reference in its entirety, and are typically contained within a sealed housing suitable for injection into the person's body. Each housing preferably contains a power source having a capacity of at least 1 microwatt-hour and power consuming circuitry preferably including a data signal transmitter and receiver and sensor/stimulator circuitry for driving an input/output transducer. Wireless communication between a system control unit (SCU) and the other implanted devices can be implemented in various ways, e.g., via a modulated sound signal, an AC magnetic field, an RF signal, a propagated electromagnetic wave, a light signal, or electrical conduction. Furthermore, in commonly owned U.S. Pat. No. 6,472,991 entitled "Multichannel Communication Protocol Configured to Extend The Battery Life Of An Implantable Device", incorporated herein by reference in its entirety, a communication protocol is described for an exemplary communication protocol for communicating between a master device (also referred to herein and in the associated patents as a system control unit (SCU)) which may be implanted within or in proximity to a person that communicates with a plurality of discrete implantable slave devices, suitable for implantation via injection, via a wireless communication channel.

Alternatively, implanted devices for use in embodiments of the present invention may be configured similarly to the devices described in the commonly owned U.S. Pat. Nos. 5,193,539 and 5,193,540 (herein referred to as the '539 and '540 patents) each of which is incorporated herein by reference in its entirety. Such devices differ from those devices described in the '284 patent in that they do not contain a battery and instead rely upon an externally-provided AC magnetic field to induce a voltage, e.g., via a coil into an internal capacitor, and thus power their internal electronics only when the external AC magnetic field is present. These devices are also referred to as being RF powered. Systems which comprise the present invention may include either the '284 battery-powered or the '539/'540 RF-powered classes of devices or combinations thereof.

In accordance with the present invention, a preferred system for prophylactically treating a person to avoid pulmonary embolisms by selectively stimulating one or more of the person's neuromuscular pathways to facilitate blood flow comprises (1) one or more implantable pulse generators configured for delivering stimulation pulses and coupling to a plurality of electrodes and suitable for placement proximate to one or more neurological pathways that respond to said stimulation pulses to facilitate blood flow; (2) a sensor for measuring a parameter corresponding to the person's movements; and wherein the one or more pulse generators periodically deliver stimulation pulses for facilitating blood flow when it is determined, according to the parameter measured by the sensor, that the person has gone through an extended period of time with limited movement.

In a further aspect of embodiments of the present invention, the parameter corresponding to the person's movements is determined by one or more accelerometers. Alternatively, the patient's movements may be determined by an electromyography (EMG) sensor that measures a signal from muscles which facilitate blood flow.

In a still further aspect of embodiments of the present invention, the system is suitable for implantation and may be contained within a sealed elongate housing having an axial dimension of less than 60 mm and a lateral dimension of less than 6 mm. Such implantable devices receive power from an externally-provided magnetic field and may contain a rechargeable battery to maintain its function during periods of time when the externally-provided magnetic field is no longer present. Alternatively, such implantable devices may rely on an externally-provided magnetic field that is supplied from a support structure, e.g., a bed or chair, that is present when the person is immobile for a relatively long length of time, e.g., inside a vehicle such as an airplane, spacecraft, military type vehicle, or wheelchair.

Finally, embodiments of the present invention may be a portion of a system of devices, e.g., a master controller and one or more implantable slave devices that may be used for restoring other motor functions to a patient having additional motor deficits.

The novel features of the invention are set forth with particularity in the appended claims. The invention will be best understood from the following description when read in conjunction with the accompanying drawings.

DETAILED DESCRIPTION OF THE PREFERRED EMBODIMENTS

Figure 1:
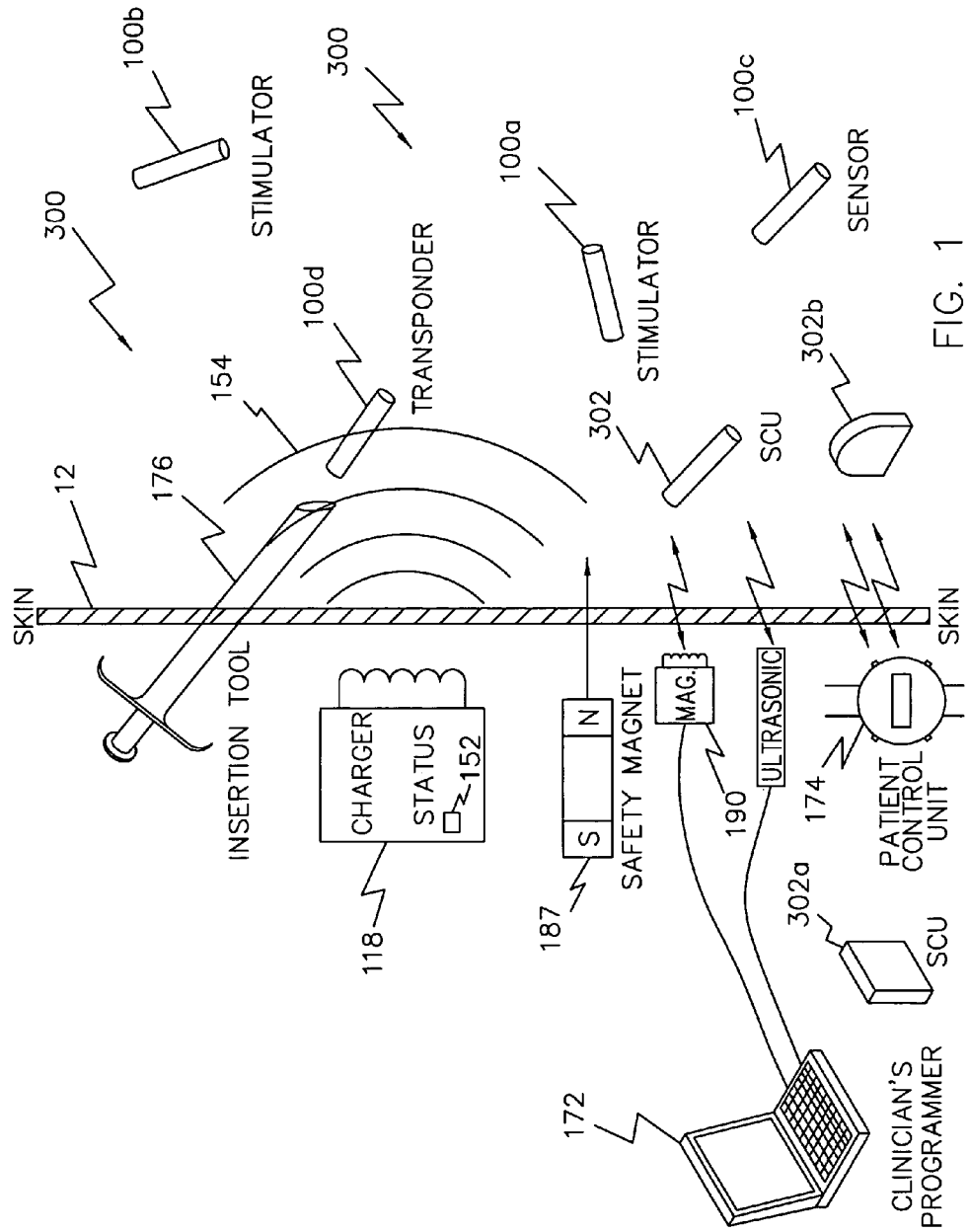
FIG. 1 is a simplified block diagram of an exemplary system suitable for practicing the present invention, the system being comprised of implanted devices, e.g., microstimulators, microsensors and microtransponders, under control of a system control unit (SCU).

The following description is of the best mode presently contemplated for carrying out the invention. This description is not to be taken in a limiting sense, but is made merely for the purpose of describing the general principles of the invention. The scope of the invention should be determined with reference to the claims.

The present invention is directed to a system and method that provide a prophylactic treatment to a person, e.g., a patient, to avoid the occurrence of pulmonary embolisms occurring as a result of deep vein thrombosis, a condition related to blood clotting in the deep veins, e.g., the iliac, femoral, popliteal, and tibial, etc., in a person's lower extremities. These veins are surrounded by powerful muscles that contract to facilitate returning blood through these veins back to the heart. When a person is inactive due to environmental conditions, e.g., prolonged sitting in an aircraft, spacecraft, military vehicle, wheelchair, etc., or due to illness or injury, e.g., paralysis, the resulting prolonged inactivity can cause the person's blood to accumulate or pool which can result in a clot that can pass to the person's lungs and cause a pulmonary embolism, a potentially fatal event. Since these undesirable conditions may occur with even a healthy person, embodiments of this invention typically refer to a person. However, persons with known medical conditions, i.e., patients, are also benefited by embodiments of the present invention. Embodiments of the present invention provide neuromuscular stimulation to a person's lower extremities, e.g., the person's legs, when the system senses that the person has been immobile for an extended period of time. An implantable neuromuscular stimulator/pacer may be used to selectively provide such stimulation. Such implantable devices are described in U.S. Pat. Nos. 5,193,539; 5,193,540; 6,164,284; 6,185,452; 6,208,894; 6,315,721; 6,564,807; and their progeny, each of which is incorporated herein by reference in its entirety. Such a device may be referred to as a BION®, a trademark of Advanced Bionics Corporation. Preferably such a device may be battery powered so that it can operate independent of an external apparatus. In particular, systems and devices of the present invention preferably include an activity monitor, e.g., an accelerometer or the like (see U.S. Pat. No. 6,466,821 which is incorporated herein by reference), that disables or limits stimulation to pronged time periods in which there is limited activity.

Implanted devices that may be adapted for use in embodiments of the present invention may be configured similarly to the devices described in the commonly owned U.S. Pat. No. 6,164,284 (hereinafter referred to as the '284 patent), incorporated herein by reference in its entirety, and are typically contained within a sealed housing suitable for injection into the person's body. Each housing preferably contains a power source having a capacity of at least 1 microwatt-hour and power consuming circuitry preferably including a data signal transmitter and receiver and sensor/stimulator circuitry for driving an input/output transducer. Wireless communication between a system control unit (SCU) and the other implanted devices can be implemented in various ways, e.g., via a modulated sound signal, an AC magnetic field, an RF signal, a propagated electromagnetic wave, a light signal, or electrical conduction. Furthermore, in commonly owned U.S. Pat. No. 6,472,991 entitled "Multichannel Communication Protocol Configured to Extend The Battery Life Of An Implantable Device", incorporated herein by reference in its entirety, a communication protocol is described for an exemplary communication protocol for communicating between a master device (also referred to herein and in the associated patents as a system control unit (SCU)) which may be implanted within or in proximity to a person that communicates with a plurality of discrete implantable slave devices, suitable for implantation via injection, via a wireless communication channel.

Alternatively, implanted devices that may be adapted for use in embodiments of the present invention may be configured similarly to the devices described in the commonly owned U.S. Pat. Nos. 5,193,539 and 5,193,540 (herein referred to as the '539 and '540 patents) each of which is incorporated herein by reference in its entirety. Such devices differ from those devices described in the '284 patent in that they do not contain a battery and instead rely upon an externally-provided AC, i.e., alternating, magnetic field to induce a voltage, e.g., via a coil into an internal capacitor, and thus power its internal electronics only when the external AC magnetic field is present. These devices are also referred to as being RF powered. Systems which comprise the present invention may include either the '284 battery-powered or the '539/'540 RF-powered classes of devices or combinations thereof.

Figure 2:
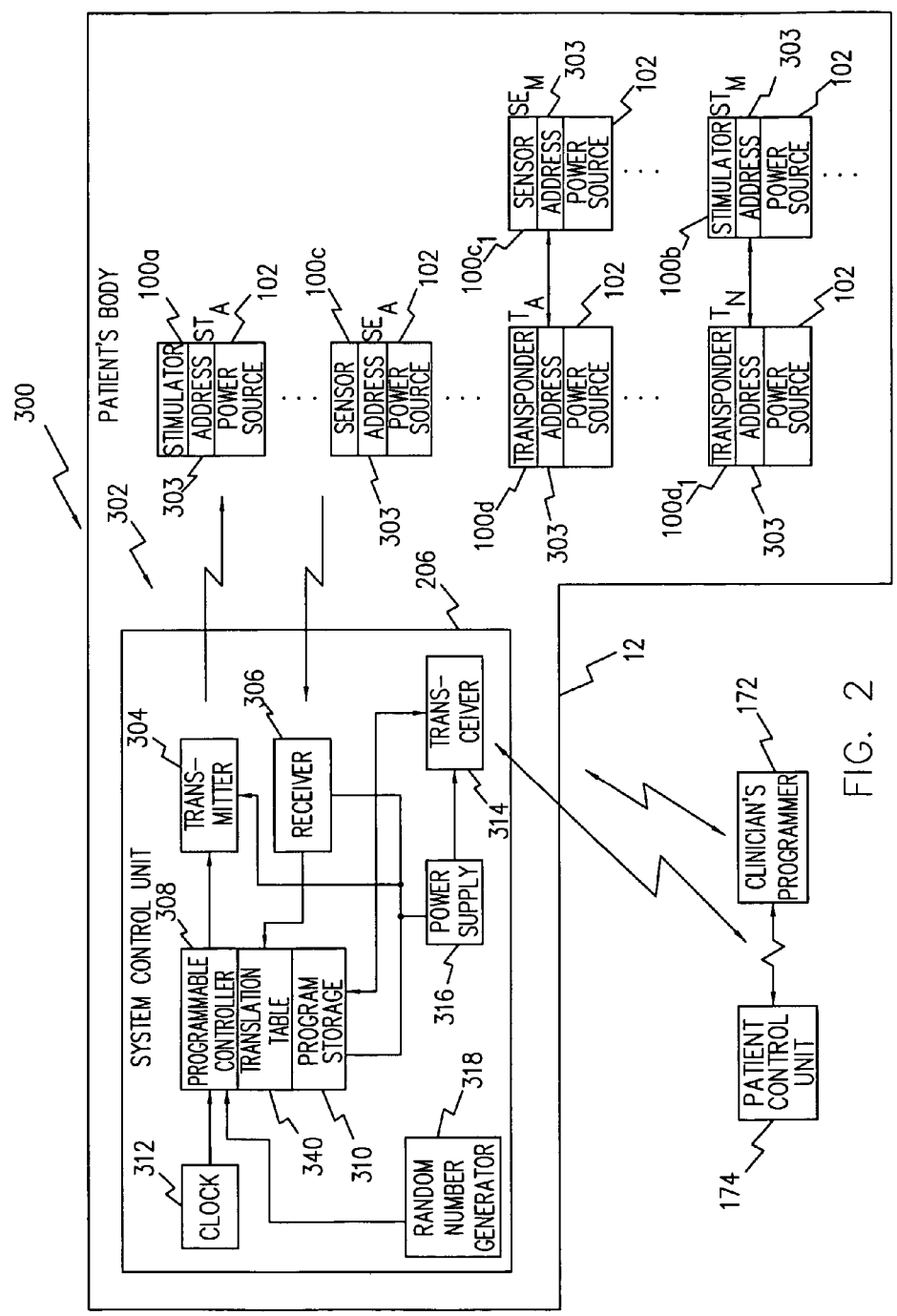
FIG. 2 comprises a block diagram of the system of FIG. 1 showing the functional elements that form the system control unit and implanted microstimulators, microsensors and microtransponders.

FIGS. 1 and 2 show an exemplary system 300 made of implanted devices 100, preferably battery powered, under control of a system control unit (SCU) 302, preferably also implanted beneath a patient's skin 12. As described in the '284 patent, potential implanted devices 100 (see also the block diagram shown in FIG. 3A) include stimulators, e.g., 100a and 100b, sensors, e.g., 100c, and transponders, e.g., 100d. The stimulators, e.g., 100a, can be remotely programmed to output a sequence of drive pulses to body tissue proximate to its implanted location via attached electrodes. The sensors, e.g., 100c, can be remotely programmed to sense one or more physiological or biological parameters in the implanted environment of the device, e.g., temperature, glucose level, $O_2$ content, nerve potential, muscle potential, etc. Transponders, e.g., 100d, are devices which can be used to extend the interbody communication range between stimulators and sensors and other devices, e.g., a clinician's programmer 172 and the patient control unit 174. Preferably, these stimulators, sensors and transponders are contained in sealed elongate housings having an axial dimension of less than 60 mm and a lateral dimension of less than 6 mm. Accordingly, such stimulators, sensors and transponders are respectively referred to as microstimulators, microsensors, and microtransponders or referred to in general as battery-powered, implantable stimulator/sensor devices. Such microstimulators and microsensors can thus be positioned beneath the skin 12 within a patient's body using a hypodermic type insertion tool 176 (see, for example commonly assigned U.S. patent application Ser. Nos. 10/116,380 and 10/116,619, respectively corresponding to U.S. Patent Application Publication Ser. Nos. 2003/0078618 and 2003/0078643, each of which is incorporated herein by reference in its entirety).

As described in the '284 patent, microstimulators and microsensors are remotely programmed and interrogated via a wireless communication channel, e.g., modulated AC magnetic, sound (i.e., ultrasonic), RF or electric fields, typically originating from control devices external to the patient's body, e.g., the clinician's programmer 172 or patient control unit 174. Typically, the clinician's programmer 172 is used to program a single continuous or one time pulse sequence into each microstimulator and/or measure a biological parameter from one or more microsensors. Similarly, the patient control unit 174 typically communicates with the implanted devices 100, e.g., microsensors 100c, to monitor biological parameters. In order to distinguish each implanted device over the communication channel, each implanted device is manufactured with a unique address or identification code (ID) 303 specified in address storage circuitry 108 (see FIG. 3A) as described in the '284 patent. Unique is a relative term, e.g., the more bits used to specify the identification code the easier it will be to distinguish one device or, in the case of master devices, one system of devices from another system of devices. Accordingly, as used in this patent application, unique is only intended to specify that the ID 303 is distinguishable from the IDs of other devices that may exist within the same environment.

By using one or more such implantable devices in conjunction with the SCU 302, the capabilities of such implanted devices can be further expanded. For example, in an open loop mode (described below in reference to FIG. 4), the SCU 302 can be programmed to periodically initiate tasks, e.g., perform real time tasking, such as transmitting commands to microstimulators according to a prescribed treatment regimen or periodically monitor biological parameters to determine a patient's status or the effectiveness of a treatment regimen. Alternatively, in a closed loop mode (described below in reference to FIGS. 5-7), the SCU 302 may periodically interrogate one or more microsensors and accordingly adjust the commands transmitted to one or more microstimulators.

FIG. 2 shows an exemplary system 300 comprised of (1) one or more implantable devices 100 operable to sense and/or stimulate a patient's body parameter in accordance with one or more controllable operating parameters and (2) the SCU 302. The SCU 302 is primarily comprised of (1) a housing 206, preferably sealed and configured for implantation beneath the skin of the patient's body, e.g., as described in the '284 patent in reference to the implanted devices 100, (2) a signal transmitter 304 in the housing 206 for transmitting command signals, (3) a signal receiver 306 in the housing 206 for receiving status signals, and (4) a programmable controller 308, e.g., a microcontroller or state machine, in the housing 206 responsive to received status signals for producing command signals for transmission by the signal transmitter 304 to other implantable devices 100. The sequence of operations of the programmable controller 308 is determined by an instruction list, i.e., a program, stored in program storage 310, coupled to the programmable controller 308. While the program storage 310 can be a nonvolatile memory device, e.g., ROM, manufactured with a program corresponding to a prescribed treatment regimen, it is preferable that at least a portion of the program storage 310 be an alterable form of memory, e.g., RAM, EEPROM, etc., whose contents can be remotely altered as described further below. However, it is additionally preferable that a portion of the program storage 310 be nonvolatile so that a default program is always present. The rate at which the program contained within the program storage 310 is executed is determined by clock/oscillator 312.

Additionally, a real time clock operating in response to clock/oscillator 312 preferably permits tasks to be scheduled at specified times of day.

The signal transmitter 304 and signal receiver 306 preferably communicate with implanted devices 100 using an RF signal, e.g., a propagated electromagnetic wave, modulated by a command data signal. Alternatively, an audio transducer may be used to generate mechanical vibrations having a carrier frequency modulated by a command data signal. In an exemplary embodiment, a carrier frequency of 100 kHz is used which corresponds to a frequency that freely passes through a typical body's fluids and tissues. However, such sound means that operate at any frequency, e.g., greater than 1 Hz, are also considered to be suitable for a potential communication channel. Alternatively, the signal transmitter 304 and signal receiver 306 can communicate using modulated AC magnetic fields.

The clinician's programmer 172 and/or the patient control unit 174 and/or other external control devices can also communicate with the implanted devices 100, as described in the '284 patent, preferably using a modulated RF or AC magnetic field. Alternatively, such external devices can communicate with the SCU 302 via a transceiver 314 coupled to the programmable controller 308. Since, the signal transmitter 304 and signal receiver 306 may operate using a different communication means, a separate transceiver 314 which operates using an alternative communication means may be used for communicating with external devices. However, a single transmitter 304/receiver 306 can be used in place of transceiver 314 for communicating with the external devices and implanted devices if a common communication channel is used.

Figure 3A:
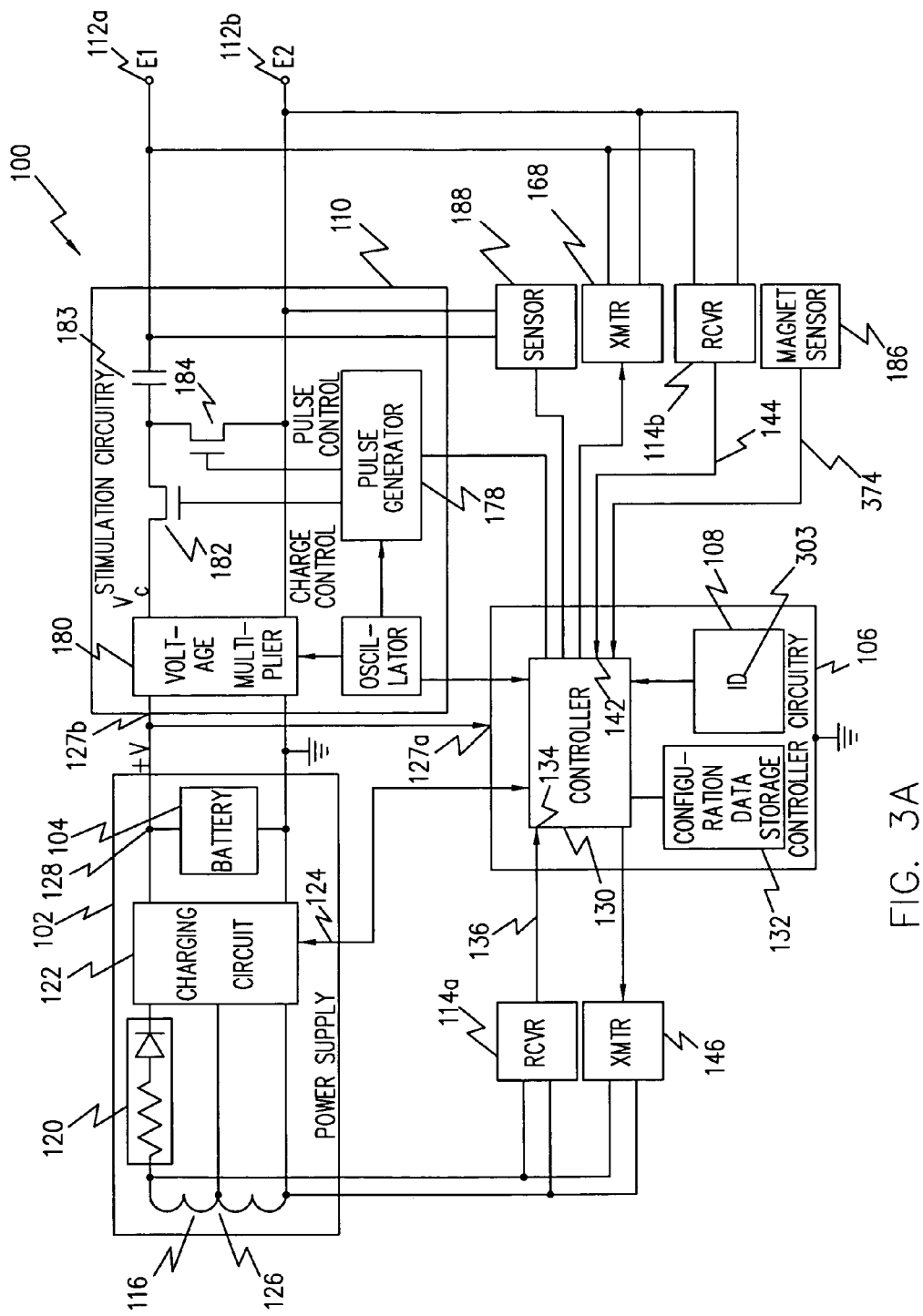
FIG. 3A comprises a block diagram of an exemplary implantable device, as shown in U.S. Pat. No. 6,164,284, including a battery for powering the device for a period of time in excess of one hour in response to a command from the system control unit.
Figure 3B:
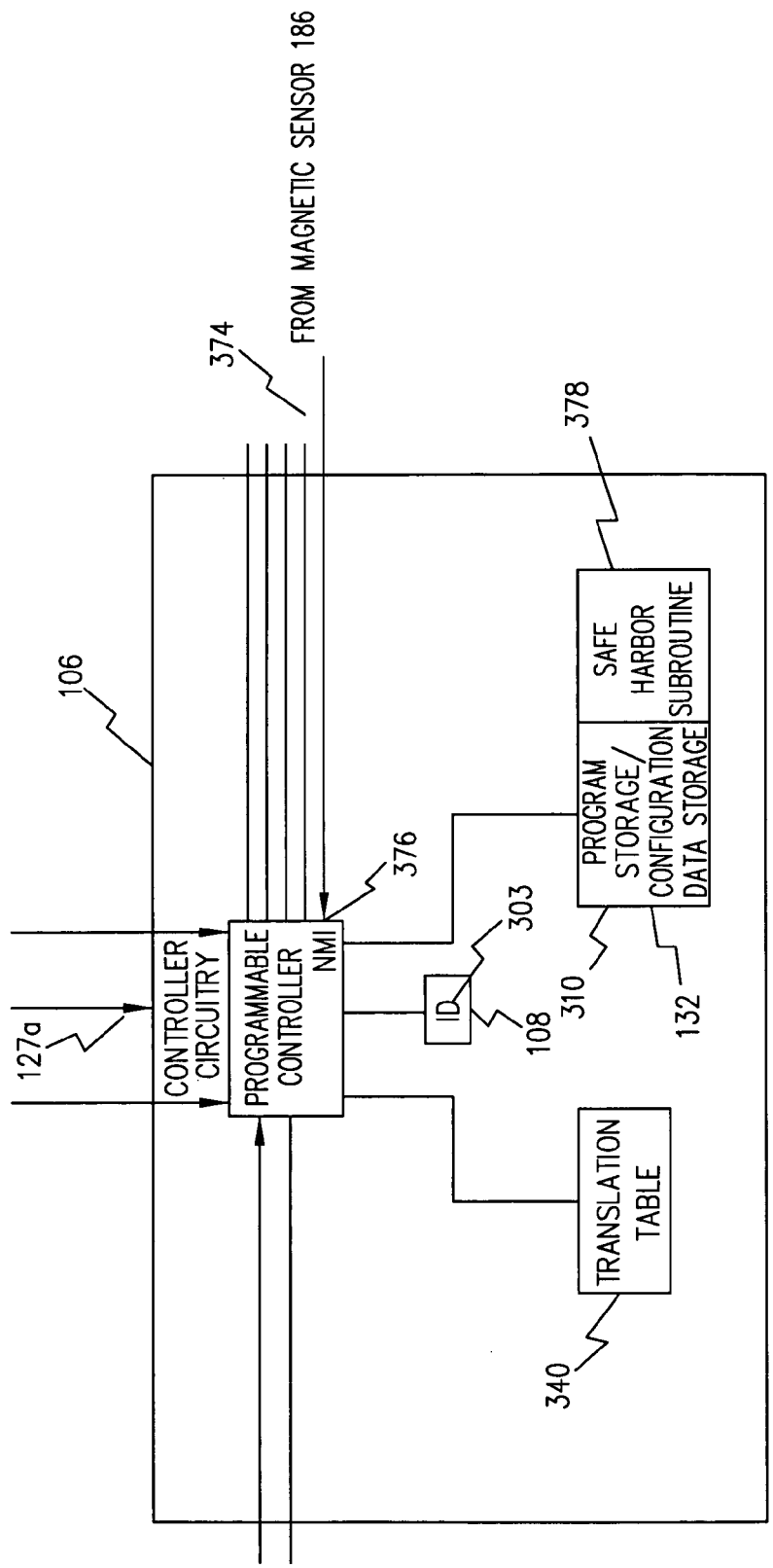
FIG. 3B comprises a simplified block diagram of controller circuitry that can be substituted for the controller circuitry of FIG. 3A, thus permitting a single device to be configured as a system control unit and/or a microstimulator and/or a microsensor and/or a microtransponder.

FIG. 3A comprises a block diagram of an exemplary implantable device 100 operable under control of controller circuitry 106 and includes a battery 104, preferably rechargeable, for powering the device for a period of time in excess of one hour and responsive to command signals from a remote master device, e.g., the SCU 302. The controller circuitry 106 is primarily comprised of a controller 130, configuration data storage 132 for prescribing its operation, and address storage circuitry 108 for storing the ID 303 of the device. As described in the '284 patent, the implantable device 100 is preferably configurable to alternatively operate as a microstimulator and/or microsensor and/or microtransponder due to the commonality of most of the circuitry contained within. Such circuitry may be further expanded to permit a common block of circuitry to also perform the functions required for the SCU 302. Accordingly, FIG. 3B shows an alternative implementation of the controller circuitry 106 of FIG. 3A that is suitable for implementing a microstimulator and/or a microsensor and/or a microtransponder and/or the SCU 302. In this implementation, the configuration data storage 132 can be alternatively used as the program storage 310 when the implantable device 100 is used as the SCU 302. In this implementation, XMTR 168 corresponds to the signal transmitter 304 and the RCVR 114b corresponds to the signal receiver 306 (preferably operable via electrodes 112a and 112b operating as an RF antenna) and the RCVR 114a and XMTR 146 correspond to the transceiver 314 (preferably operable via coil 116 for AC magnetic modes of communication).

Preferably, the contents of the program storage 310, i.e., the software that controls the operation of the programmable controller 308, can be remotely downloaded, e.g., from the clinician's programmer 172 using data modulated onto an RF signal or an AC magnetic field. In this mode, it is preferable that the contents of the program storage 310 for each SCU 302 be protected from an inadvertent change. Accordingly, the contents of the address storage circuitry 108, i.e., the ID 303, is preferably used as a security code to confirm that the new program storage contents are destined for the SCU 302 receiving the data. This feature is particularly significant if multiple patients could be physically located, e.g., in adjoining beds, within the communication range of the clinician's programmer 172.

Preferably, the SCU 302 can operate for an extended period of time, e.g., in excess of one hour, from an internal power supply 316 (see FIG. 2). While a primary battery, i.e., a nonrechargeable battery, is suitable for this function, it is preferable that the power supply 316 include a rechargeable battery, e.g., battery 104 as described in the '284 patent, that can be recharged via an AC magnetic field produced external to the patient's body. Accordingly, power supply 102 of FIG. 3A is the preferred power supply 316 for the SCU 302 as well.

The battery-powered devices 100 of the '284 patent are preferably configurable to operate in a plurality of operational modes, e.g., via a communicated command signal. In a first operational mode, device 100 is remotely configured to be a microstimulator, e.g., 100a and 100b. In this embodiment (see FIG. 3A), controller 130 commands stimulation circuitry 110 to generate a sequence of drive pulses through electrodes 112 to stimulate tissue, e.g., a nerve or muscle, proximate to the implanted location of the microstimulator, e.g., 100a or 100b. In operation, a programmable pulse generator 178 and voltage multiplier 180 are configured with parameters corresponding to a desired pulse sequence and specifying how much to multiply (or divide) the battery voltage (e.g., by summing charged capacitors or similarly charged battery portions) to generate a desired compliance voltage $V_c$. A first FET 182 is periodically energized to store charge into capacitor 183 (in a first direction at a low current flow rate through the body tissue) and a second FET 184 is periodically energized to discharge capacitor 183 in an opposing direction at a higher current flow rate which stimulates a nearby muscle or nerve. Alternatively, electrodes can be selected that will form an equivalent capacitor within the body tissue.

In a next operational mode, the battery-powered implantable device 100 can be configured to operate as a microsensor, e.g., 100c, that can sense one or more physiological or biological parameters in the implanted environment of the device. In accordance with a preferred mode of operation, the system control unit 302 periodically requests the sensed data from each microsensor 100c using its ID 303 stored in the address storage circuitry 108, and responsively sends command signals to microstimulators, e.g., 100a and 100b, adjusted according to the sensed data. For example, sensor circuitry 188 can be coupled to the electrodes 112 to sense or otherwise used to measure a biological parameter, e.g., temperature, glucose level, $O_2$ content, voltage, current, impedance, etc., and provide the sensed data to the controller circuitry 106. Preferably, the sensor circuitry 188 includes a programmable bandpass filter and an analog to digital (A/D) converter that can sense and accordingly convert the voltage levels across the electrodes 112 into a digital quantity. Alternatively, the sensor circuitry 188 can include one or more sense amplifiers to determine if the measured voltage exceeds a threshold voltage value or is within a specified voltage range. Furthermore, the sensor circuitry 188 can be configurable to include integration circuitry to further process the sensed voltage. The operational mode of the voltage sensor circuitry 188 is remotely programmable via the device's communication interface. See, for example, the circuitry described in U.S. patent application Ser. No. 10/121,881 (corresponding to U.S. Patent Application Publication No. 2003/0195578) which is incorporated herein by reference in its entirety. In embodiments of the present invention, this circuitry may be coupled to the muscles surrounding the person's deep veins to sense depolarization and thus whether there has been adequate stimulation to avoid accumulating of blood and related forming of blood clots (emboli) that could migrate to the person's lungs, resulting in a pulmonary embolism.

Additionally, the sensing capabilities of a microsensor preferably include the capability to monitor the battery status via path 124 from the charging circuit 122 and can additionally include using an ultrasonic transducer, i.e., emitter/receiver (not shown), or the coil 116 to respectively measure the ultrasonic, magnetic or propagated RF signal magnitudes (or communication time delays) of signals transmitted between a pair of implanted devices and thus determine the relative locations of these devices. This information can be used to determine the amount of body movement, e.g., the amount that an elbow or finger is bent, and thus form a portion of a closed loop motion control system.

In another operational mode, the battery-powered implantable device 100 can be configured to operate as a microtransponder, e.g., 100d. In this operational mode, the microtransponder receives (via the aforementioned RCVR 114a using AC magnetic, sonic, RF, or electric communication modes) a first command signal from the SCU 302 and retransmits this signal (preferably after reformatting) to other implanted devices (e.g., microstimulators, microsensors, and/or microtransponders) using the aforementioned XMTR 168 using magnetic, sonic, RF, or electric communication modes. While a microtransponder may receive one mode of command signal, e.g., magnetic, it may retransmit the signal in another mode, e.g., RF. For example, clinician's programmer 172 may emit a modulated magnetic signal using a magnetic emitter 190 (see FIG. 1) to program/command the implanted devices 100. However, the magnitude of the emitted signal may not be sufficient to be successfully received by all of the implanted devices 100. As such, a microtransponder 100d may receive the modulated magnetic signal and retransmit it (preferably after reformatting) as a modulated ultrasonic or RF signal which can pass through the body with fewer restrictions. In another exemplary use, the patient control unit 174 may need to monitor a microsensor 100c in a patient's foot. Despite the efficiency of ultrasonic, magnetic, and propagated RF communication in a patient's body, such a signal could still be insufficient to pass from a patient's foot to a patient's wrist (the typical location of the patient control unit 174). As such, a microtransponder 100d could be implanted (if needed) in the patient's torso to improve the communication link.

Figure 4:
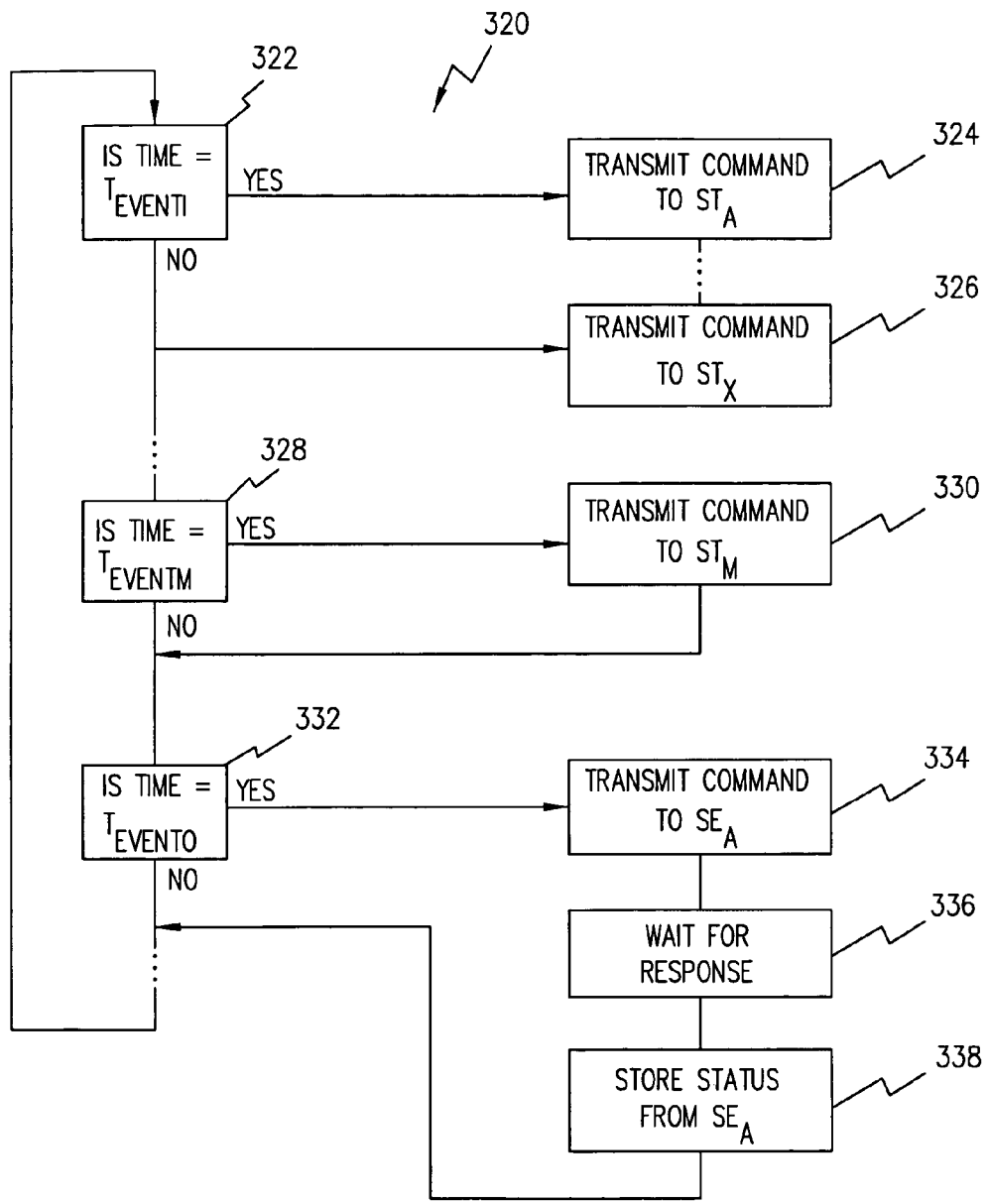
FIG. 4 shows an exemplary flow chart of the use of an exemplary system in an open loop mode for controlling/monitoring a plurality of implanted devices, e.g., microstimulators, microsensors.

FIG. 4 shows a block diagram of an exemplary open loop control program, i.e., a task scheduler 320, for controlling/monitoring a body function/parameter. In this process, the programmable controller 308 is responsive to the clock 312 (preferably a crystal controlled oscillator to thus permit real time scheduling) in determining when to perform any of a plurality of tasks. In this exemplary flow chart, the programmable controller 308 first determines in block 322 if it is now at a time designated as $T_{EVENT1}$ (or at least within a sampling error of that time), e.g., at 1:00 AM. If so, the programmable controller 308 transmits a designated command to microstimulator A ($ST_A$) in block 324. In this example, the control program continues where commands are sent to a plurality of stimulators and concludes in block 326 where a designated command is sent to microstimulator X ($ST_X$). Such a subprocess, e.g., a subroutine, is typically used when multiple portions of body tissue require stimulation, e.g., stimulating a plurality of muscle groups in a paralyzed limb to avoid atrophy. The task scheduler 320 continues through multiple time event detection blocks until in block 328, it determines whether the time $T_{EVENTM}$ has arrived. If so, the process continues at block 330 where, in this case, a single command is sent to microstimulator M ($ST_M$). Similarly, in block 332, the task scheduler 320 determines when it is the scheduled time, i.e., $T_{EVENTO}$, to execute a status request from microsensor A ($SE_A$). If so, a subprocess, e.g., a subroutine, commences at block 334 where a command is sent to microsensor A ($SE_A$) to request sensor data and/or specify sensing criteria. Microsensor A ($SE_A$) does not instantaneously respond. Accordingly, the programmable controller 308 waits for a response in block 336. In block 338, the returned sensor status data from microsensor A ($SE_A$) is stored in a portion of the memory, e.g., a volatile portion of the program storage 310, of the programmable controller 308. The task scheduler 320 can be a programmed sequence, i.e., defined in software stored in the program storage 310, or, alternatively, a predefined function controlled by a table of parameters similarly stored in the program storage 310. A similar process may be used where the SCU 302 periodically interrogates each implantable device 100 to determine its battery status.

Figure 5:
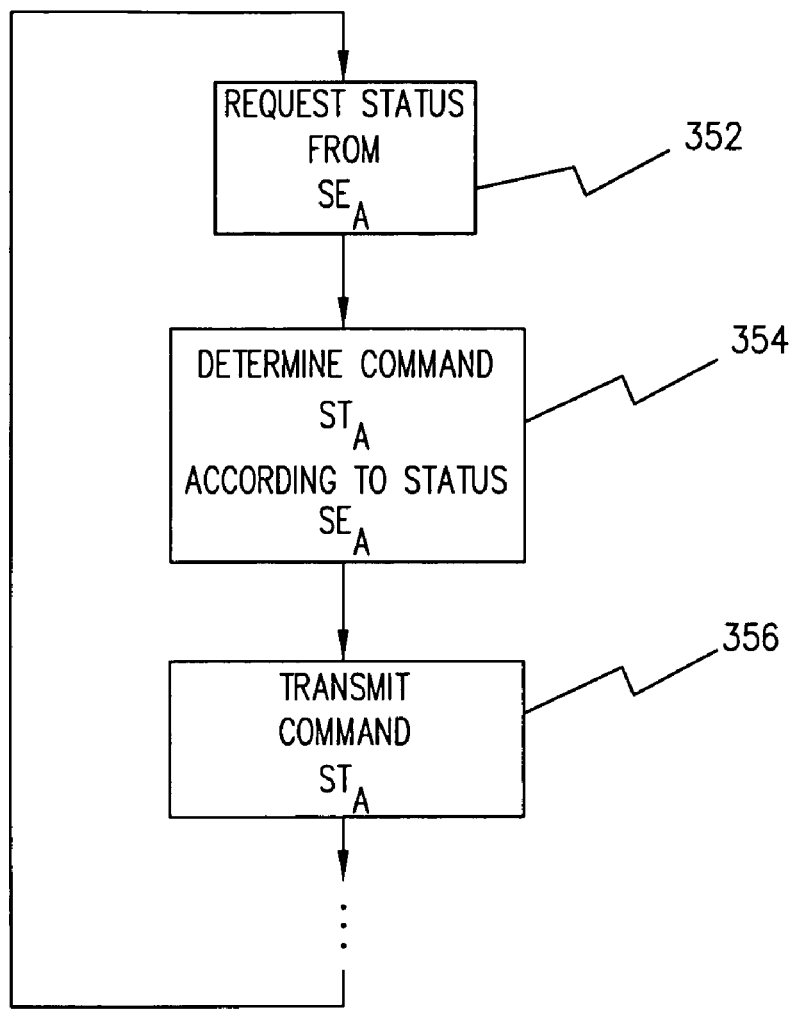
FIG. 5 shows a simplified flow chart of the use of closed loop control of a microstimulator by altering commands from the system control unit in response to status data received from a microsensor.

FIG. 5 is an exemplary block diagram showing the use of such a system to perform closed loop control of a body function. In block 352, the SCU 302 requests status from microsensor A ($SE_A$). The SCU 302, in block 354, then determines whether the present command given to a microstimulator is satisfactory and, if necessary, determines a new command and transmits the new command to the microstimulator A ($ST_A$) in block 356. For example, if microsensor A ($SE_A$) is reading a voltage corresponding to the degree of contraction resulting from stimulating a muscle, the SCU 302 could transmit a command to microstimulator A ($ST_A$) to adjust the sequence of drive pulses, e.g., in magnitude, duty cycle, etc., and accordingly change the voltage sensed by microsensor A ($SE_A$). Accordingly, closed loop, i.e., feedback, control is accomplished. The characteristics of the feedback (proportional, integral, derivative (PID)) control are preferably program controlled by the SCU 302 according to the control program contained in program storage 310.

Figure 6:
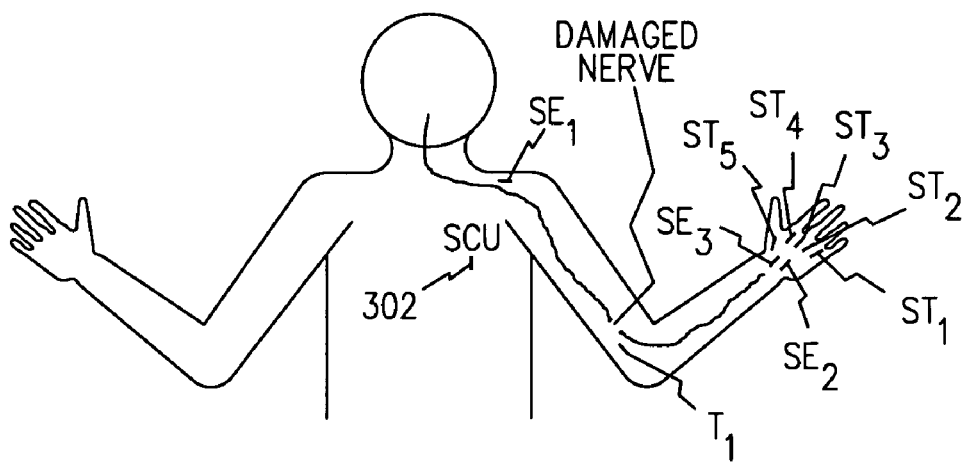
FIG. 6 shows an exemplary injury, i.e., a damaged nerve, and the placement of a plurality of implanted devices, i.e., microstimulators, microsensors and a microtransponder under control of the system control unit for "replacing" the damaged nerve.

FIG. 6 shows an exemplary injury treatable by such an exemplary system 300. In this exemplary injury, the neural pathway has been damaged, e.g., physically or effectively (as a consequence of a stroke or the like) severed, just above the patient's left elbow. The goal of this exemplary system is to bypass the damaged neural pathway to permit the patient to regain control of the left hand. An SCU 302 is implanted within the patient's torso to control a plurality of stimulators, $ST_1$-$ST_5$, implanted proximate to the muscles respectively controlling the patient's thumb and fingers (shown in the patient's hand for simplicity). Additionally, microsensor 1 ($SE_1$) is implanted proximate to an undamaged nerve portion where it can sense a signal generated from the patient's brain when the patient wants hand closure. Optional microsensor 2 ($SE_2$) is implanted in a portion of the patient's hand where it can sense a signal corresponding to stimulation/motion of the patient's pinky finger and microsensor 3 ($SE_3$) is implanted and configured to measure a signal corresponding to grip pressure generated when the fingers of the patient's hand are closed. Additionally, an optional microtransponder ($T_1$) is shown which can be used to improve the communication between the SCU 302 and the implanted devices.

Figure 7:
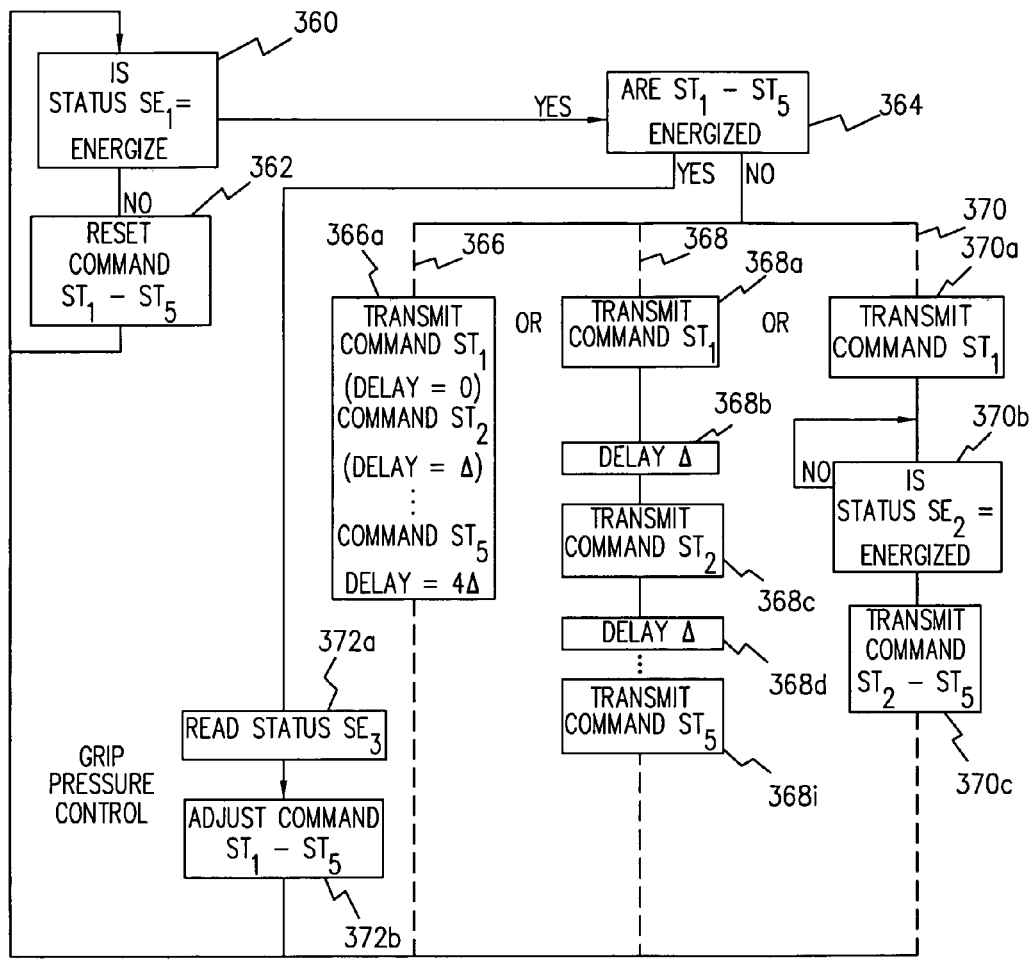
FIG. 7 shows a simplified flow chart of the control of the implanted devices of FIG. 6 by the system control unit.

FIG. 7 shows an exemplary flow chart for the operation of the SCU 302 in association with the implanted devices in the exemplary system of FIG. 6. In block 360, the SCU 302 interrogates microsensor 1 ($SE_1$) to determine if the patient is requesting actuation of his fingers. If not, a command is transmitted in block 362 to all of the stimulators ($ST_1$-$ST_5$) to open the patient's hand, i.e., to de-energize the muscles which close the patient's fingers. If microsensor 1 ($SE_1$) senses a signal to actuate the patient's fingers, the SCU 302 determines in block 364 whether the stimulators $ST_1$-$ST_5$ are currently energized, i.e., generating a sequence of drive/stimulation pulses. If not, the SCU 302 executes instructions to energize the stimulators. In a first optional path 366, each of the stimulators is simultaneously (subject to formatting and transmission delays) commanded to energize in block 366a. However, the command signal given to each one specifies a different start delay time. Accordingly, there is a stagger between the actuation/closing of each finger.

In a second optional path 368, the microstimulators are consecutively energized by a delay Δ. Thus, microstimulator 1 ($ST_1$) is energized in block 368a, a delay is executed within the SCU 302 in block 368b, and so on for all of the microstimulators. Accordingly, paths 366 and 368 perform essentially the same function. However, in path 366 the interdevice timing is performed by the clocks within each implanted device 100 while in path 368, the SCU 302 is responsible for providing the interdevice timing.

In path 370, the SCU 302 actuates a first microstimulator ($ST_1$) in block 370a and waits in block 370b for its corresponding muscle to be actuated, as determined by microsensor 2 ($SE_2$), before actuating the remaining stimulators ($ST_2$-$ST_5$) in block 370c. This implementation could provide more coordinated movements in some situations.

Once the stimulators have been energized, as determined in block 364, closed loop grip pressure control is performed in blocks 372a and 372b by periodically reading the status of microsensor 3 ($SE_3$) and adjusting the commands given to the stimulators ($ST_1$-$ST_5$) accordingly. Consequently, this exemplary system has enabled the patient to regain control of his hand including coordinated motion and grip pressure control of the patient's fingers.

Referring again to FIG. 3A, a magnetic sensor 186 is shown. In the '284 patent, it was shown that such a sensor 186 could be used to disable the operation of an implanted device 100, e.g., to stop or otherwise alter the operation of such devices in an emergency situation, in response to a DC magnetic field, preferably from an externally positioned safety magnet 187 (see FIG. 1). Additionally, it is noted that power to at least some portions of a preferred implantable device may be removed when a magnetic field is sensed and thus power may be conserved. The magnetic sensor 186 can be implemented using various devices. Exemplary of such devices are devices manufactured by Nonvolatile Electronics, Inc. (e.g., their AA, AB, AC, AD, or AG series), Hall effect sensors, magnetoresistive sensors, and subminiature reed switches. Such miniature devices are configurable to be placed within the housing of the SCU 302 and implantable devices 100. While essentially passive magnetic sensors, e.g., reed switches, are possible, the remaining devices may include active circuitry that consumes power during detection of the DC magnetic field. Accordingly, it is preferred that controller 130 periodically, e.g., once a second, provide power to the magnetic sensor 186 and sample the magnetic sensor's output signal 374 during that sampling period. Additionally, a magnetoresistive sensor is especially preferred due to its small size that enables its use within the preferred implantable device 100 while conserving the available internal package volume.

The battery 104 used for powering the implantable device 100 (or SCU 302) is made from appropriate materials so as to preferably provide a power capacity of at least 1 microwatt-hour. Preferably, such a battery, e.g., a Li-I battery, has an energy density of about 240 mw-Hr/cm$^3$. The battery voltage V of an exemplary battery is nominally 3.6 volts, which is more than adequate for operating the CMOS circuits preferably used to implement the IC chip(s) 216, and/or other electronic circuitry, within the SCU 302.

The battery 104 may take many forms, any of which may be used so long as the battery can be made to fit within the small volume available. The battery 104 may be either a primary battery or a rechargeable battery. A primary battery offers the advantage of not requiring a recharging circuit and the disadvantage of not being rechargeable (which means once its energy has been used up, the implanted device no longer functions).

A preferred system for forming the environment for use of the present invention is comprised of an implanted SCU 302 and a plurality of implanted devices 100, each of which contains its own rechargeable battery 104. As such, a patient is essentially independent of any external apparatus between battery chargings (which generally occur no more often than once an hour and preferably no more often than once every 24 hours). However, for some treatment regimens, it may be adequate to use a power supply analogous to that described in commonly assigned U.S. Pat. No. 5,324,316 (herein referred to as the '316 patent and incorporated by reference in its entirety) that only provides power while an external AC magnetic field is being provided, e.g., from charger 118. Additionally, it may be desired, e.g., from a cost or flexibility standpoint, to implement the SCU 302 as an external device, e.g., within a watch-shaped housing that can be attached to a patient's wrist in a similar manner to the patient control unit 174.

The power consumption of the SCU 302 is primarily dependent upon the circuitry implementation, preferably CMOS, the circuitry complexity and the clock speed. For a simple system, a CMOS implemented state machine will be sufficient to provide the required capabilities of the programmable controller 308. However, for more complex systems, e.g., a system where an SCU 302 controls a large number of implanted devices 100 in a closed loop manner, a microcontroller may be required. As the complexity of such microcontrollers increases (along with its transistor count), so does its power consumption. Accordingly, a larger battery having a capacity of 1 to 10 watt-hours is preferred. While a primary battery is possible, it is preferable that a rechargeable battery be used. Such larger batteries will require a larger volume and accordingly, cannot be placed in the injectable housing described above.

Since only one SCU is required to implement a system, the battery life of the SCU may be accommodated by increasing the casing size (e.g., increasing at least one dimension to be in excess of 1 inch) for the SCU to accommodate a larger sized battery and either locating a larger SCU 302a (see FIG. 1) external to patient's body or a larger SCU 302b may be surgically implanted.

Essentially, there have been described two classes of implantable devices 100, a first which is typically referred to as being RF powered, i.e., it does not contain a battery but instead receives all of its operating power from an externally-provided AC magnetic field (which field is preferably modulated to additionally wirelessly communicate commands to the implantable devices 100), and a second class which is referred to as battery powered which is powered by an internally provided battery which, in turn, is preferably rechargeable and periodically recharged by a similar externally-provided magnetic field (see, for example, commonly assigned U.S. patent application Ser. No. 10/272,229 corresponding to U.S. Patent Application Publication No. 2003/0078634, which is incorporated herein by reference in its entirety, which describes recharging environments and techniques for use with such implantable devices) but preferably receives its wireless commands via a modulated RF signal. Thus, in this case, the wireless command signal may be distinct from the wireless charging signal. However, in most other ways, these two classes of implantable devices are similar, e.g., they have similar size restrictions, are suitable for implantation via injection, and can similarly stimulate neural pathways and, thus, they are accordingly generally interchangeable in embodiments of the present invention its and environments. Alternatively, embodiments of the present invention may include combinations of RF and battery-powered devices to take advantage of differences, e.g., cost and functional, between both classes of devices.

There are various techniques used by embodiments of the present invention to determine the need to increase blood flow in a person to avoid deep vein thrombosis. In a first class of techniques, physical movements of the person are sensed with an accelerometer 380 or the like. Since an accelerometer may show momentary peaks, e.g., impulse movements from movements/bumps of a vehicle that is carrying the person, may not correspond to whether the patient has actually moved sufficiently to facilitate blood flow, i.e., to limit blood pooling. Thus, it is preferable that the output of the accelerometer 380 be filtered, e.g., low pass filtered, to remove such a momentary increase. Such filtering may be done in either the analog domain, i.e., a hardware filter, or in the digital domain, e.g., via a software filter. Such filtering techniques are well known and need no further explanation here. Additionally, the use of multiple, e.g., multi-axis, accelerometers may be used to determine the nature of the movement and a weighted, e.g., hardware or software, average of its inputs may be used to determine if the sensed movement has adequately reflected sufficient patient movement to avoid deep vein thrombosis. Accordingly, in the referenced figures, a referenced accelerometer 380 coupled to the controller 130 of FIG. 3A may also correspond to a plurality of accelerometers and may also include filtering circuitry or associated software (or such circuitry or associated software may be included within the controller 130 that responds to the accelerometer inputs). Exemplary embodiments of such single and multi-axis accelerometers are found in U.S. Pat. No. 6,466,821 (describing a multi-axis implementation) and U.S. patent application Ser. Nos. 10/758,366 (corresponding to U.S. Patent Application Publication No. 2004/0153127), Ser. No. 10/365,893 (corresponding to U.S. Patent Application Publication No. 2004/0158294), and Ser. No. 10/805,043 (corresponding to U.S. Patent Application Publication No. 2004/0183607), each of which is incorporated by reference in its entirety.

While it is particularly desirable to inject one or more of the aforedescribed devices in locations suitable to directly, i.e., using integral electrodes 112a, 112b, stimulate the muscles surrounding the deep veins and thereby facilitate blood flow, it may be desirable to couple leaded electrodes to implantable devices 100 to stimulate desired neural pathways. Thus, commonly assigned U.S. patent application Ser. No. 09/971,849 (corresponding to U.S. Patent Application Publication Ser. No. 2002/0193859) and Ser. No. 09/971,848, now U.S. Pat. No. 6,738,672, the contents of which are incorporated herein by reference in their entirety and referred to herein as the leaded BION® patents (note, BION® is a registered trademark of Advanced Bionics Corporation), are particularly relevant in that they describe techniques for attaching leads to the aforedescribed implantable devices that can then be connected, e.g., via lead splices when necessary, to leaded electrodes, which may be coupled to neural pathways suitable for stimulating the muscles surrounding the aforementioned deep veins and thereby increase blood flow.

Figure 8:
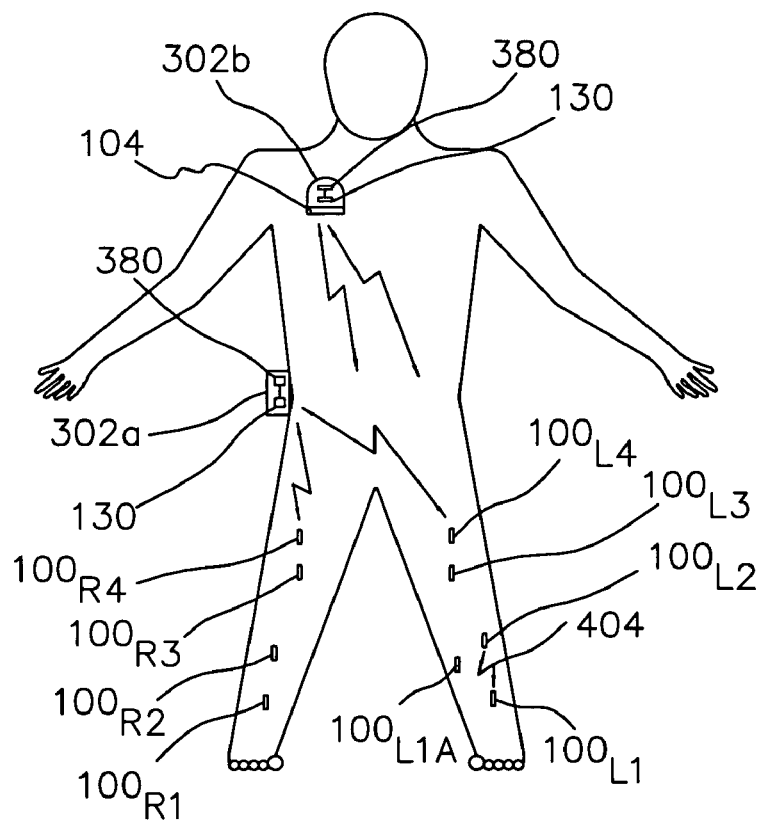
FIG. 8 shows a simplified exemplary placement of one or more implantable, preferably injectable, stimulators, i.e., neurostimulators, placed proximate to muscles surrounding the person's deep veins, e.g., iliac, femoral, popliteal, tibial, etc., in the person's legs to facilitate blood flow.
Figure 8:
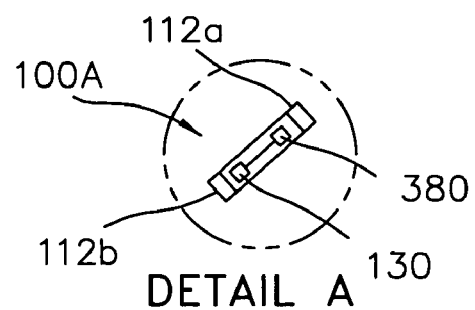

FIG. 8 shows a simplified exemplary placement of one or more implantable injectable, stimulators 100 placed proximate to muscles surrounding the person's deep veins, e.g., iliac, femoral, popliteal, tibial, etc., in the person's legs to facilitate blood flow. In particular, stimulators $100_{L1}$-$100_{L4}$ are shown in the person's right leg and $100_{R1}$-$100_{R4}$ are shown in the person's right leg. Preferably, the stimulators are sized (as previously described) such that they may be implanted via injection. By using injectable implantation, this opens up the solution provided by embodiments of the present invention to be made available to large number of potentially vulnerable individuals, e.g., soldiers or individuals who have had prior attacks, that are periodically subjected to an environment that increases the risk factors for a pulmonary embolism.

Figure 9:
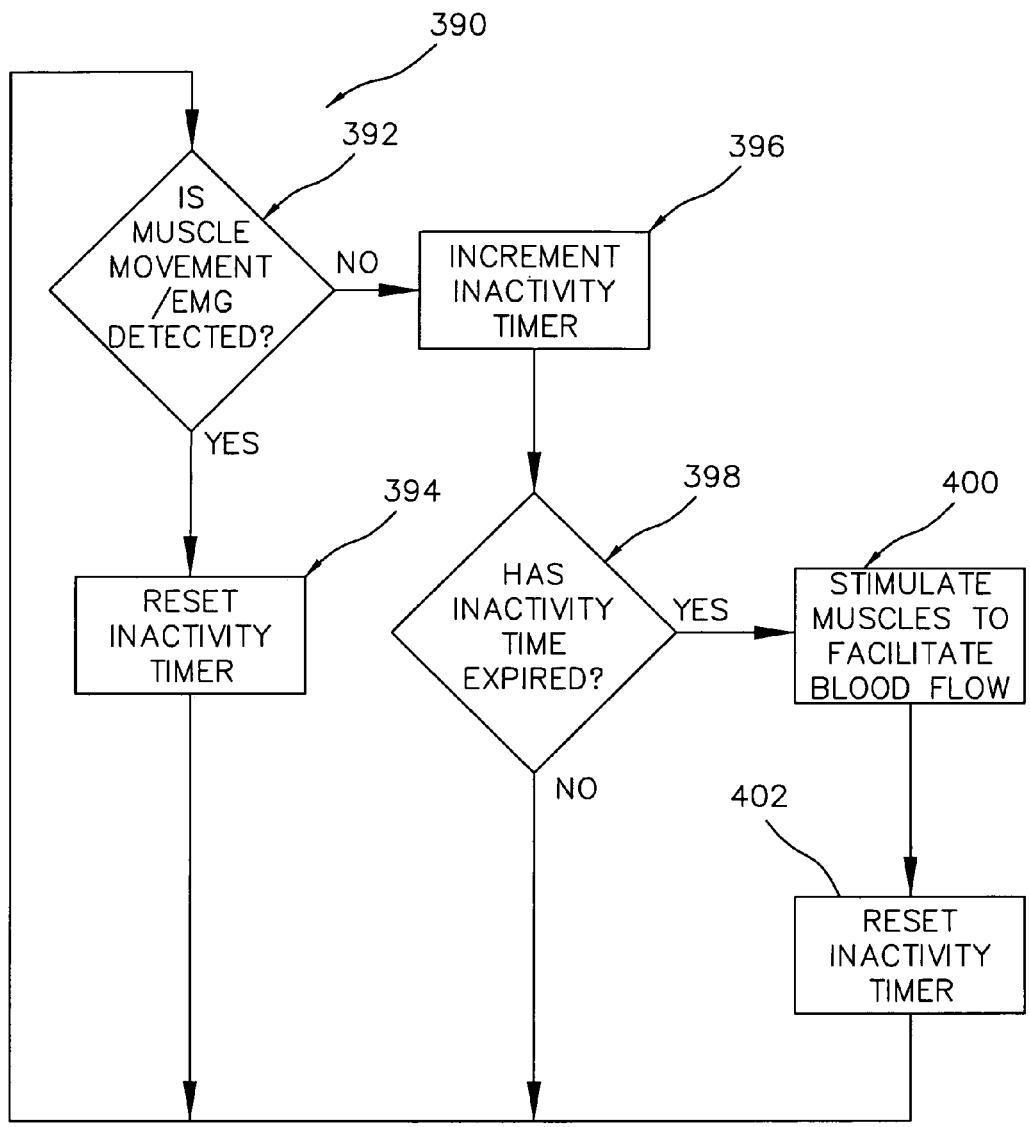
FIG. 9 shows a simplified flow chart of the operation of the implantable stimulators that cause the stimulators to stimulate muscles that surround the person's deep veins when it is determined, e.g., according to the absence of movement of detected EMG signals, that blood flow in the person's lower extremities should be increased as a prophylactic treatment for pulmonary embolisms.

In a first preferred embodiment, each implantable device 100 contains an accelerometer 380 that is coupled to its internal controller 130 (see also FIG. 3A). Additionally in this first preferred embodiment, the controller 130 operates according to an algorithm, somewhat analogous to that of a watchdog timer (which is typically implemented with a retriggerable one shot), that provides stimulation whenever sufficient movement has not been detected for a prolonged time period. For example, FIG. 9 shows a simplified flow chart 390 of the operation of the implantable stimulators 100 that cause the stimulators to stimulate muscles surround the person's deep veins when it is determined, e.g., according to the absence of movement or detected EMG signals, that blood flow in the person's lower extremities should be increased as a prophylactic treatment for pulmonary embolisms. These operations may be accomplished by a pure hardware, pure software, or combination hardware/software implementation. Accordingly under control of controller 130, movement of the person is determined in block 392 using accelerometer 380. Alternatively, the EMG of the associated muscles can be measured by sensor 188 (see FIG. 3A) to determine adequate movement and/or stimulation of the associated muscles that facilitate blood flow. If adequate movement/EMG (preferably subject to a low pass filter to remove sensitivity to external or minimal signals) is measured, an inactivity timer is reset in block 394 and the process repeats with block 392. If inadequate movement and/or stimulation of the associated muscles is not detected, an inactivity timer (typically a software register in controller 130) is incremented in block 396 and in block 398, it is determined whether the inactivity timer has expired. If the inactivity timer has not expired, the process repeats at block 392. If the inactivity timer has expired, the selected muscles are stimulated in block 400. The inactivity timer is then reset in block 402 and the process continues at block 392.

In this first preferred embodiment, the implantable device 100 is of the battery-powered type of the '284 patent and uses battery 104 (see FIG. 3A) which is periodically recharged. Accordingly, once the device's battery is charged, the device may always be active. (Alternatively, a primary i.e., a non-rechargeable, battery may be used when period of immobility will be limited a relatively short period of vulnerability and thus the device will no longer need to be active after the primary battery has expired.) In an analogous fashion to an implantable defibrillator, no stimulation will occur unless it is needed. Therefore, the person will not be aware of the stimulator's presence unless, due to lack of movement, it emits one or more stimulation pulses. Even then, this programmed stimulation may not be noticed (depending on the stimulation settings) by the person.

In a second preferred embodiment, not all of the implantable devices will have the movement sensor, i.e., accelerometer 380 or EMG sensor 188 (see FIG. 3A). For example, implantable device $100_{L1}$ may have a movement sensor and operate and as a master device that may communicate via a wireless link 404 to other implantable devices 100 that are without movement sensors or do not rely upon their movement sensors. Alternatively, multiple implantable devices 100 may contain a movement sensor but these additional movement sensors may be held in reserve in case the movement sensor in the first device, e.g., $100_{L1}$, fails. Finally, implantable device $100_{L1A}$ may serve solely as a movement sensor and/or master device and the remaining devices may provide the stimulation signals. Additionally, as previously described, stimulation signals emitted from implantable devices may be programmably staggered to achieve a desired result and this may additionally facilitate blood flow when the implantable devices are located to stimulate different muscle or muscle portions along the person's deep veins.

Figure 10:
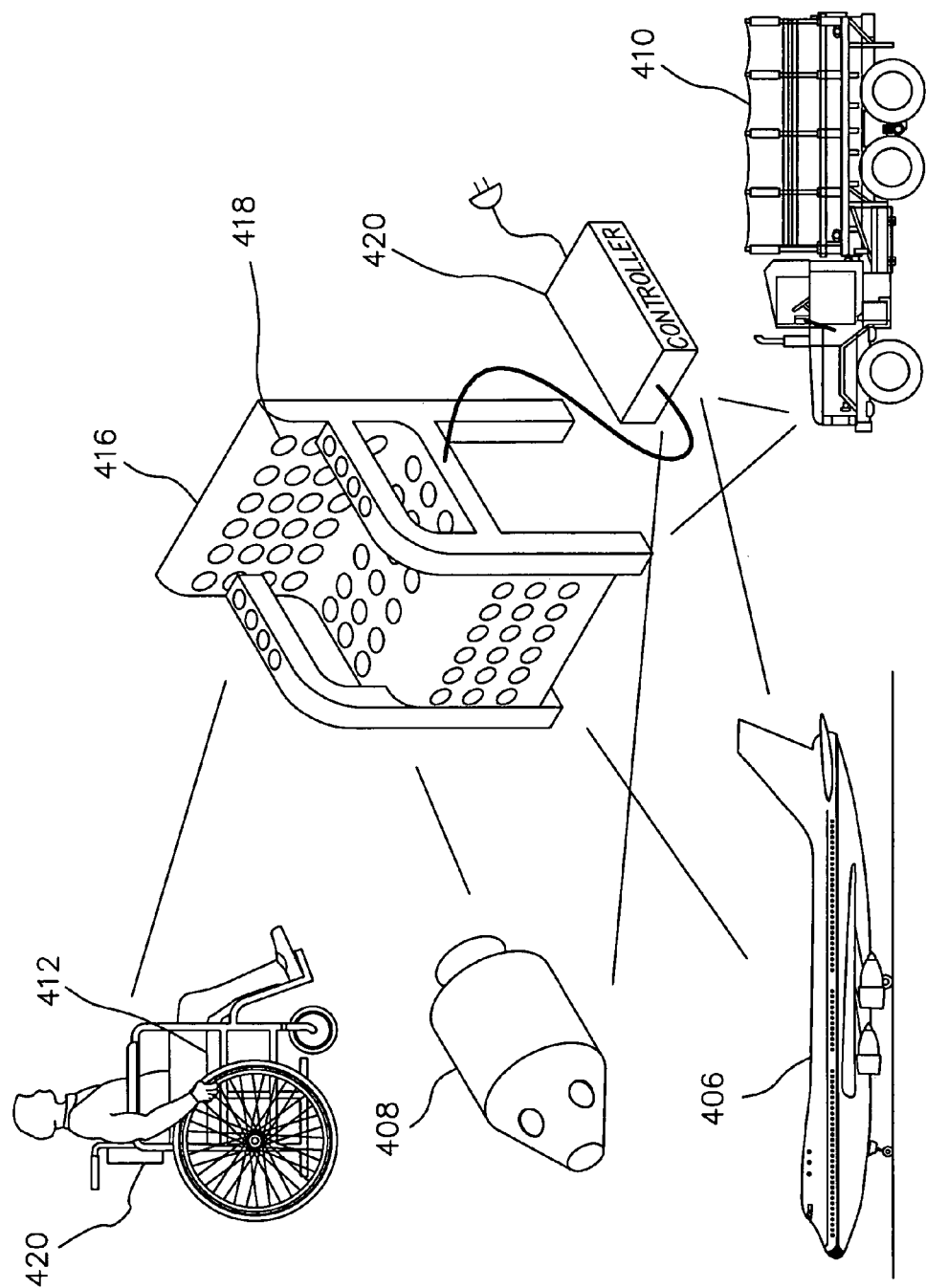
FIG. 10 shows exemplary vehicles, e.g., an airplane, a spacecraft, military vehicle, or wheelchair, where the person's movements are potentially limited for extended periods of time. To remedy the potential formations of emboli and a subsequent pulmonary embolism, a support structure, e.g., a chair, is located within the vehicle to supply power and/or control signals to the implantable devices which periodically, preferably according to predicted need, stimulate muscles surrounding the person's deep veins.

In a third preferred embodiment, the implantable devices 100 may be of the RF-powered type of the '539/'540 patents. In this embodiment, the implantable devices 100 are inoperative unless an AC, i.e., alternating, magnetic field is present. However, since the need for the present invention generally relates to the person being in a restricted position and location, this restricted position and location, e.g., in a vehicle such as an airplane 406, a spacecraft 408, military type vehicle 410, wheelchair 412, etc., (see FIG. 10), may contain a support structure 414, e.g., a chair 416, (having one or more coils 418 contained within) and a controller 420 that powers the coils 418 to generate the AC magnetic field and may additionally provide a control signal which may modulate the AC magnetic field or may generate an RF signal, i.e., controller 420 may be a combination of the functionality of one or more of the charger 118, clinician's programmer 172 and magnetic emitter 190, and patient control unit 174 (see FIG. 3A). The controller 420 may be internally powered via a battery (not shown) or externally powered via coupling to an AC or DC power source. Note that in the case of a wheelchair 412, the support structure 414 may contain the internal coils 418 and the controller 420, i.e., the wheelchair operates as a vehicle and a support structure 414. In a first variation of the third embodiment, the controller 420 may only function as a generator of the AC magnetic field and in this case, this embodiment would be functionally equivalent to that described in the first two alternative embodiments. In a next variation, one or more of the implantable devices 100 may communicate back to the controller 420 operating as a master controller (functionally equivalent to the clinician's programmer 172 or patient control unit 174) that monitors the person's movement and/or muscle depolarization using an EMG sensor and responsively causes the implantable devices 100 to emit stimulation pulses when required as described in reference to the flow chart of FIG. 9.

In a next variation of the third embodiment, it is recognized that the susceptibility to pulmonary embolisms is increased whenever the person is confined to this support structure 414 for a sustained period of time. Accordingly, the system may operate open loop and the controller may supply an AC magnetic field to power the implantable devices 100 that are pre-programmed to periodically generate stimulation pulses at a constant rate separated by prolonged predefined periods of time, i.e., preemptively without directly sensing the lack of movement. Alternatively, controller 420 may both supply an AC magnetic field to the implantable device 100 and periodically (separated by a prolonged predefined period of time) emit a wireless (modulated magnetic or RF signals) command to cause the implantable devices to generate stimulation pulses. Each of these implementations may provide stimulation pulse when they are not needed. For example, if a person periodically gets up from their seat in an airplane and walks around, they may not need any additional muscle stimulation. Accordingly, when an implantable device is selected that enables a bidirectional communication interface to exist between the controller 420 and the implantable devices 100, the absence and presence of the implantable devices 100 and thus the person may be detected. Accordingly, a timer in the controller 420 may be reset each time that the person sits down and/or stands up, e.g., for a sufficient period of time.

Figure 11:
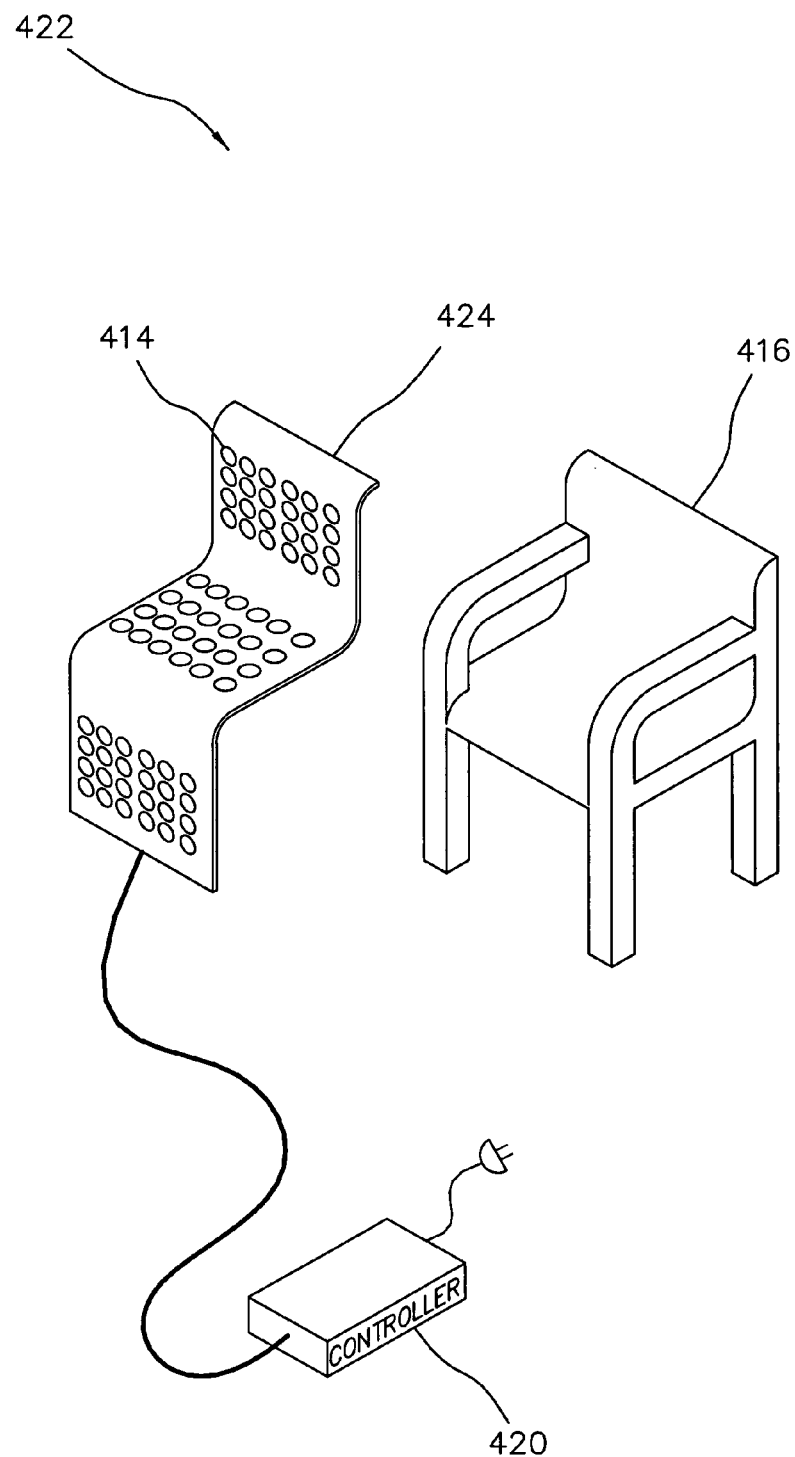
FIG. 11 shows an alternative device to the support structure of FIG. 10 is shown where coils are in a pad that may be placed upon the support structure, e.g., a chair, allowing the present system to operate in an environment that does not otherwise provide direct functional support for the implantable devices.

The support structure 414, e.g., a chair 416, need not have integral coils 418. Accordingly, FIG. 11 shows an alternative embodiment 422 to the support structure 414 of FIG. 10 where the coils 418 are in a pad 424 that may be placed upon a support structure, e.g., a chair 416, bed or mattress 426, etc., allowing the present system to operate in an environment that would not otherwise provide direct functional support for the implantable devices, i.e., a standard chair could be used.

Figure 12:
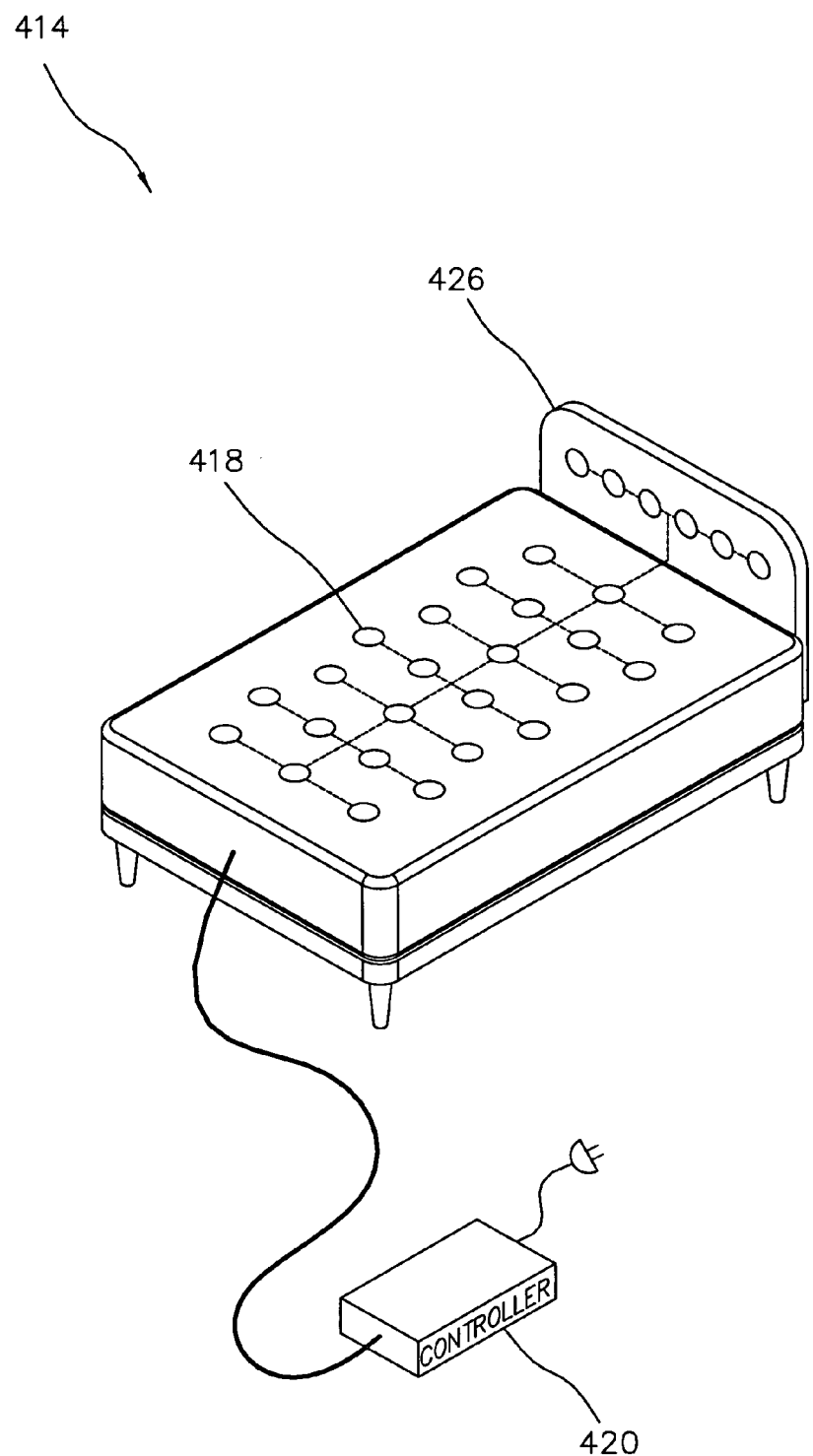
FIG. 12 shows an exemplary support structure, e.g., a bed or mattress that, includes a plurality of coils implanted within or on, e.g., in a pad as in FIG. 11, that can alternatively supply recharging power or operating power to the implantable devices. This structure is of particular use to a patient confined to a bed, e.g., a paralyzed patient.
Figure 13:
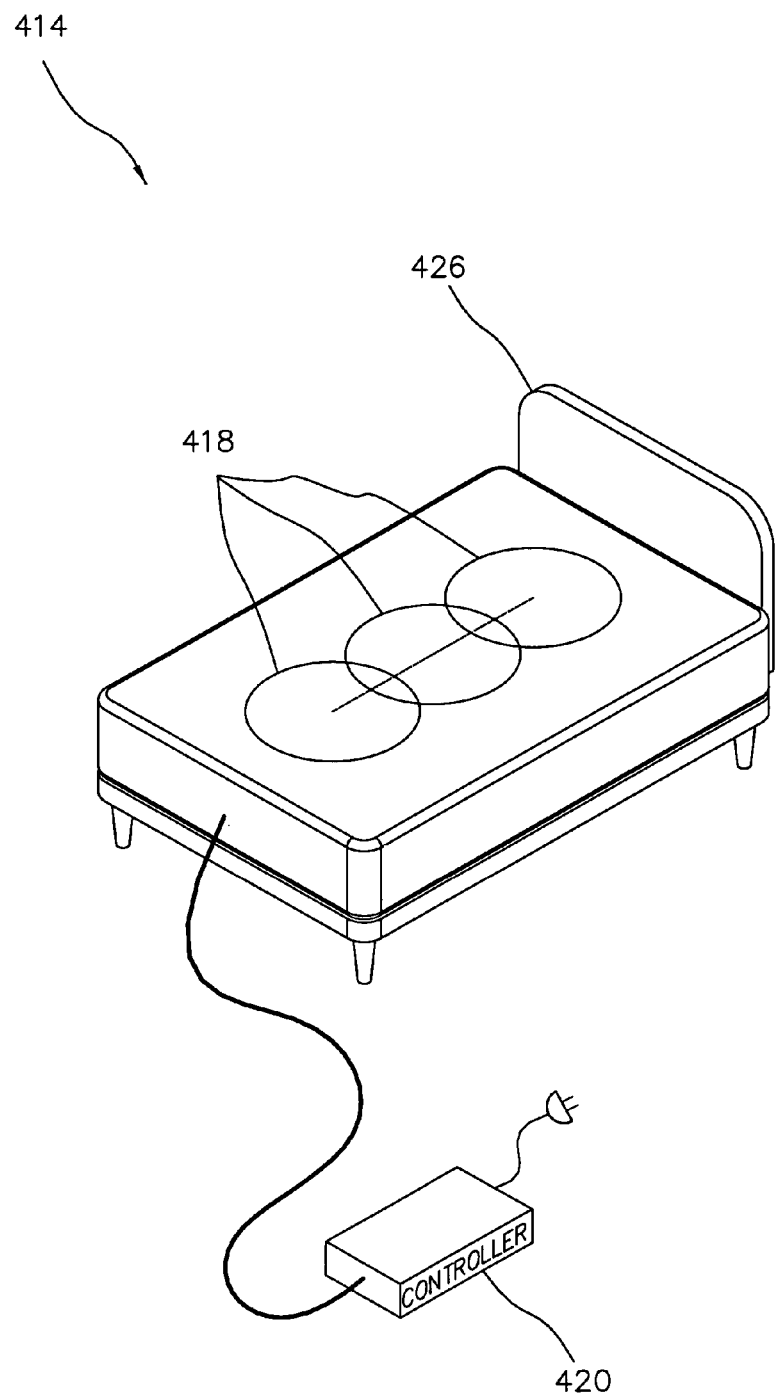
FIG. 13 shows and alternative implementation of the support structure of FIG. 12 that differs to the extent that it employs fewer but larger coils with overlapping fields.

Finally, rechargeable battery type devices as described in the '284 patent will require periodic recharging. Accordingly, FIG. 12 shows an exemplary support structure, e.g., a bed or mattress 426 that, includes a plurality of coils 418 implanted within or on, e.g., in a pad 424 as in FIG. 11, that can alternatively supply recharging power or operating power to the implantable devices. This structure is of particular use to patient confined to a bed, e.g., a paralyzed patient, and in other aspects operates similar to the support structure of FIG. 10. FIG. 13 shows and alternative implementation of the support structure of FIG. 12 that differs to the extent that it employs fewer but larger coils with overlapping fields.

Accordingly, what has been shown is a system and method that provides a prophylactic treatment to avoid occurrence of pulmonary embolisms by periodic stimulation of neuromuscular pathways in a patient to facilitate blood flow, e.g., in the patient's lower extremities, preferably when the system senses that the patient has been immobile for extended periods of time. While the invention has been described by means of specific embodiments and applications thereof, it is understood that numerous modifications and variations could be made thereto by those skilled in the art. For example, while the prior descriptions of the present invention have been primarily directed toward prophylactically treating pulmonary embolisms, the present invention may be a portion of a larger system that treats additional medical problems, e.g., replaces or treats neurological deficits. Accordingly, embodiments which use an external 302a or internal 302b SCU which additionally communicate with other portions of the patient's body (see FIGS. 1, 6, and 8) are also considered to be within the scope of the present invention. Accordingly, such variations may be made without departing from the spirit and scope of the invention. It is therefore to be understood that within the scope of the claims, the invention may be practiced otherwise than as specifically described herein.

What is claimed is:

1. A method for prophylactically treating a person to avoid pulmonary embolisms by using an implantable electronic device, said electronic device utilizing wireless communications and configured to selectively stimulate one or more of a person's neuromuscular pathways to facilitate blood flow, said method comprising the steps of:
   automatically and sequentially measuring, at predetermined incremented times a parameter corresponding to the person's movements; comprising:
      incrementing a timer in the absence of the persons movements; and
      determining if the timer has reached a predetermined period of time; and
   periodically stimulating one or more of the person's neurological pathways utilizing at least one implanted electronic device to facilitate blood flow for avoiding pulmonary embolisms when it is determined according to said measured parameter that the person has gone through the predetermined period of time with limited movements.

2. The method of claim 1 wherein said step of periodically measuring a parameter corresponding to the person's movements comprises measuring the person's movements using one or more accelerometers.

3. The method of claim 1 wherein said step of periodically measuring a parameter corresponding to the person's movements comprises measuring the person's movements using two or more accelerometers oriented at approximately right angles to each other and said step of periodically stimulating one or more of the person's neurological pathways to facilitate blood flow comprises periodically stimulating one or more of the person's neurological pathways to facilitate blood flow according to weighted measurements from said two or more accelerometers.

4. The method of claim 1 wherein said step of periodically measuring a parameter corresponding to the person's movements comprises periodically measuring EMG signals from one or more muscles associated with facilitating blood flow.

5. A system for prophylactically treating a person to avoid pulmonary embolisms by selectively stimulating one or more of the person's neuromuscular pathways to facilitate blood flow, said system comprising:
one or more implantable pulse generators, said one or more implantable pulse generators utilizing wireless communications and configured for delivering stimulation pulses and coupling to a plurality of electrodes suitable for placement proximate to one or more neurological pathways that respond to said stimulation pulses to facilitate blood flow;
a sensor for measuring a parameter corresponding to the person's movements;
an inactivity timer configured to be incremented in the absence of the person's movements, said inactivity timer including means to determine whether the inactivity timer has reached a predetermined period of time; and
wherein said one or more pulse generators periodically deliver stimulation pulses for facilitating blood flow when it is determined according to said parameter measured by said sensor that the person has gone through the predetermined period of time with limited movement.

6. The system of claim 5 wherein said movement sensor comprises one or more accelerometers.

7. The system of claim 5 wherein said movement sensor comprises an EMG sensor.

8. The system of claim 5 wherein said movement sensor comprises two or more accelerometers oriented at approximately right angles to each other; and wherein
delivery of said stimulation pulses is periodically determined according to weighted measurements from said two or more accelerometers.

9. The system of claim 5 wherein said one or more pulse generators are contained within a sealed elongate housing having an axial dimension of less than 60 mm and a lateral dimension of less than 6 mm that is suitable for implantation within the person's body.

10. The system of claim 5 wherein said sensor and at least one of said pulse generators are contained within a sealed elongate housing having an axial dimension of less than 60 mm and a lateral dimension of less than 6 mm that is suitable for implantation within the person's body.

11. The system of claim 10 additionally comprising: a master controller in periodic wireless communication with said one or more pulse generators and said movement sensor; and wherein said master controller periodically determines the need to facilitate blood flow in response to said measured parameter from said movement sensor and communicates said determination to said one or more pulse generators.

12. The system of claim 11 wherein said master controller is suitable for implantation within the person's body.

13. The system of claim 11 wherein said master controller is configured for use external to the person's body.

14. The system of claim 11 wherein said master controller additionally comprises said sensor for measuring a parameter corresponding to the person's movement.

15. The system of claim 5 comprising at least two implantable devices each contained within a sealed elongate housing having an axial dimension of less than 60 mm and a lateral dimension of less than 6 mm wherein each of said implantable devices has at least one pulse generator contained within and at least one of said implantable devices contains said sensor for measuring a parameter corresponding to the person's movements and wherein said implantable devices communicate with each other and thereby coordinate operations.

16. The system of claim 5 additionally comprising: a master controller in periodic wireless communication with said one or more pulse generators and said movement sensor; and wherein said master controller periodically determines the need to facilitate blood flow in response to said measured parameter from said movement sensor and communicates said determination to said one or more pulse generators.

17. The system of claim 5 additionally comprising: a master controller; a plurality of implantable devices suitable for stimulation of neurological pathways, wherein each of said implantable devices is contained within a sealed elongate housing having an axial dimension of less than 60 mm and a lateral dimension of less than 6 mm and is under control of wireless signals from said master controller; and wherein said one or more pulse generators are implantable and under control of said master controller.

18. The system of claim 17 wherein said master controller is implantable.

19. The system of claim 5 additionally comprises a power source for supplying power to said one or more pulse generators and said sensor.

20. The system of claim 19 wherein said power source comprises a rechargeable battery configured for receiving recharging power from an externally-provided alternating magnetic field.

21. The system of claim 19 wherein said power source comprises a capacitor for receiving power from an externally-provided alternating magnetic field.

22. The system of claim 21 wherein said externally-provided alternating magnetic field is provided from a user support structure.

23. The system of claim 22 wherein said user support structure is selected from the group of a chair, a bed, and a wheelchair.

24. The system of claim 22 wherein said user support structure is configured for placement within a vehicle.

25. The system of claim 24 wherein said vehicle is selected from the group of a airplane, a military type vehicle, and a spacecraft.

26. The system of claim 21 wherein said externally-provided alternating magnetic field is provided from a pad configured for placement on a user support structure.

\* \* \* \* \*